United States Patent
Mohanty et al.

(10) Patent No.: US 8,571,365 B2
(45) Date of Patent: Oct. 29, 2013

(54) APPARATUS AND METHOD FOR MICROMANIPULATION OF MICROSCALE OBJECTS USING LASER LIGHT DELIVERED THROUGH A SINGLE OPTICAL FIBER AND AXICON LENS

(75) Inventors: Samarendra K. Mohanty, Irvine, CA (US); Jared Stephens, Oceanside, CA (US); Michael W. Berns, Bonsall, CA (US)

(73) Assignee: The Regents of the University of California, Oakland, CA (US)

( * ) Notice: Subject to any disclaimer, the term of this patent is extended or adjusted under 35 U.S.C. 154(b) by 869 days.

(21) Appl. No.: 12/613,472

(22) Filed: Nov. 5, 2009

(65) Prior Publication Data

US 2010/0120113 A1    May 13, 2010

Related U.S. Application Data

(60) Provisional application No. 61/111,596, filed on Nov. 5, 2008.

(51) Int. Cl.
*G02B 6/26* (2006.01)
*G02B 6/42* (2006.01)

(52) U.S. Cl.
USPC .................. 385/38; 606/15; 606/16; 606/17; 385/33; 604/20; 604/21

(58) Field of Classification Search
None
See application file for complete search history.

(56) References Cited

U.S. PATENT DOCUMENTS

| | | | | |
|---|---|---|---|---|
| 5,370,643 | A | * | 12/1994 | Krivoshlykov et al. .......... 606/16 |
| 7,285,744 | B2 | * | 10/2007 | Chen ......................... 219/121.63 |
| 2004/0114860 | A1 | * | 6/2004 | Dultz et al. ...................... 385/31 |
| 2012/0135368 | A1 | * | 5/2012 | Rizoiu et al. .................... 433/29 |

* cited by examiner

*Primary Examiner* — Uyen Chau N Le
*Assistant Examiner* — Chad Smith
(74) *Attorney, Agent, or Firm* — Marcus C. Dawes; Daniel L. Dawes (57) ABSTRACT

A single optical fiber having a distal end is optically coupled to the laser and distilling terminated with an axicon lens optically coupled to the single optical fiber to form a microscopic distal tip to provide a spatially shaped elongated laser focused spot for microprocessing and/or microdissection of a microscale object. A pulsed or continuous laser beam or superposition of pulsed and continuous laser beams is generated, controllably spatially shaped, selectively oriented, selectively moved via movement of a single optical fiber terminated with the axicon lens, and the oriented, spatially shaped laser beam applied via the single optical fiber terminated with the axicon lens to a living or nonliving microscopic object for manipulation, micro-dissection, alteration/ablation, and excitation of the living or nonliving microscopic object.

8 Claims, 10 Drawing Sheets
(2 of 10 Drawing Sheet(s) Filed in Color)

APPARATUS AND METHOD FOR MICROMANIPULATION OF MICROSCALE OBJECTS USING LASER LIGHT DELIVERED THROUGH A SINGLE OPTICAL FIBER AND AXICON LENS

RELATED APPLICATIONS

The present application is related to U.S. Provisional Patent Application Ser. No. 61/111,596, filed on Nov. 5, 2008, which is incorporated herein by reference and to which priority is claimed pursuant to 35 USC 119.

BACKGROUND OF THE INVENTION

1. Field of the Invention

The invention relates to the field of single-fiber optical tweezers and scissors enabled in-depth multi-functional micro-manipulation of cells.

2. Description of the Prior Art

Optical scissors and tweezers have been tools of the biologist for over two decades. Laser scissors uses lasers to alter and/or to ablate intracellular organelles and cellular and tissue samples, and today have become an important tool for cell biologists to study the molecular mechanism of complex biological systems. Single cells or groups of cells have been perforated for injection of exogenous materials, induction of DNA damage in cells, micro-dissection of neuronal processes as well as other intra-cellular organelles such as chromosomes, microtubules. Clinically, it has also been used to reduce the thickness of the zona pellucida layer of the ovum in order to improve human in vitro fertility. In all these applications, either a scanning stage or scanning mirror was used to scan a region in a single cell or group of cells for microprocessing.

Optical manipulation of microscopic objects using spatially sculptured optical landscapes coupled with optical binding is gaining considerable interest for engineering self-assembled colloidal and biological structures. While far-field binding between microscopic objects has been demonstrated using elliptical beams or two counter propagating beams, near-field trapping and binding over a large area has been reported at the interface of total internal reflection (TIR) occurring in a prism. Except for two fiber trapping, all other approaches have depth limitation. The two-fiber configuration requires critical alignment of the two counter propagating beams and therefore restricts three-dimensional (3D) manipulation of the optically bound structure. Theoretical evaluation of the trapping force exerted by the microfocused beam from an axicon-tipped single fiber and its use for in-depth trapping of cells and low-index particles has been demonstrated recently. An axicon (having a conical distal or terminal surface) can be used to turn a Gaussian beam into a Bessel beam, with greatly reduced diffraction and smallest optical confinement zones. The micro-axicon fiber can trap at a larger distance from the fiber tip compared to a tapered fiber.

Recently, the application of optically based micromanipulation has led to an explosion of new applications. In particular, optical tweezers and scissors have had a major impact on the fields of biophysics and colloidal science with applications ranging from measurement of force at the single molecule level to disease diagnosis to therapeutic applications in the field of assisted reproductive therapy.

Recently, while optical tweezers have been shown to enhance and guide neuronal growth, femtosecond laser scissors have been employed for axotomy of neurons, allowing measurement of the regeneration process. In contrast to the short working distance of the high numerical aperture, NA, microscope objectives, optical tweezers and scissors based on a single optical fiber will enable micromanipulation at much larger depths and thus open up additional avenues for biophysics and nanoscience research.

While no report exists on single-fiber scissors, earlier attempts to trap in three dimensions using a single optical fiber have not been successful, even with a hemispherical lens built on the tip of fiber. This failure is presumably due to the dominance of the scattering force in the axial direction. While particle trapping using a single fiber probe with an annular light distribution required balance of opposing optical and electrostatic forces, recently, pure-optical 3-D trapping was demonstrated using a tapered and axicon-tip fiber.

The short working distance of microscope objectives have severely restricted the application of optical tweezers and scissors at larger depths. Therefore, there is a growing attention towards use of optical fibers for manipulation of microscopic objects. Recently, in-depth single fiber optic trapping of low as well as high index particles has been demonstrated using micro-axicon tip fibers. The shaping the axicon tip cone angle enabled fiber optic trapping in near-field. Further, we have demonstrated controlled guidance of neuronal growth cones as well as trapping and stretching of neurons using the fiber-optic tweezers. The cells could be stretched by combined action of two forces, an attractive gradient force due to fiber optic tweezers at high beam powers pulling the membrane and a scattering force on the membrane as reported in dual fiber trapping. Alignment of intra-cellular dark (high refractive index) material along the direction of laser beam propagation was also observed. By mode-locking, the fiber-optic tweezers beam was converted to fiber-optic scissors, enabling dissection of neuronal processes. This microscopic-controlled nano-dissection of neurons followed by a process of resealing and repair could serve as a useful tool for basic and applied studies on neuronal damage, repair and regeneration. At reduced average power of the femtosecond fiber-optic microbeam, microinjection of impermeable exogenous materials into the trapped cells was also possible. At high average powers, lysis of a three-dimensionally trapped cell was accomplished.

BRIEF SUMMARY OF THE INVENTION

The illustrated embodiment of the present invention is a simple-to-operate device which uses a spatially shaped elongated laser focused spot for micro-dissection of living/nonliving microscopic objects with high throughput. In the past, either a scanning stage or scanning mirror was used to scan a region in a single cell or group of cells for microprocessing and/or microdissection. Besides being expensive, the prior art approach requires complex control of the scanning beam via computer. Most importantly, the above mentioned techniques require large processing time for groups of cells. This reduces the throughput of the laser microbeam system. Further, this may lead to the requirement of immobilization (by optically trapping or otherwise) of the motile object(s) for precise micro-dissection.

The illustrated embodiment of the invention is a device and method that uses a spatially shaped laser beam (generated simply by insertion of a cylindrical lens) for manipulation, micro-dissection, alteration/ablation, and excitation of living or nonliving microscopic objects with high throughput. To achieve the spatial shaped laser beam, the $N_2$ pulsed UV-laser beam was focused to a linear profile by use of a cylindrical lens. For optical trapping of the objects in suspension, a CW NIR laser beam was also aligned with the UV laser scissors beam by use of a dichroic mirror. This elongated UV (and or NIR) laser beam was relayed to the back aperture of a high NA Zeiss microscope objective via the epi-fluorescence port. The cylindrical lens was mounted on a motorized rotational stage so as to enable controlled orientation of the direction of elongation in the x-y plane. A variable aperture (VAP) was placed at the focal plane of the cylindrical lens in order to control the length of the focused spot. For fluorescence imaging, light from a mercury lamp was collimated and coupled to the microscope by use of a dichroic mirror that reflects UV (and or NIR), but transmits the visible region of the mercury spectrum. The excitation filter was placed in a filter wheel and another dichroic mirror was used to reflect the fluorescence excitation light, the 337 nm laser scissors beam and optionally the laser tweezers beam. This dichroic mirror transmitted the emitted fluorescence as well as the transmitted halogen light from the sample in the sample chamber. The emission filter also blocked the UV laser scissors and NIR laser tweezers beam. The dimensions of the generated elliptical focused spot determine the length over which the object(s) can be dissected and/or trapped. Use of a 50 mm focal length cylindrical lens in our setup led to a focal spot length of ~40/µm at the object plane. The intensity pattern of the elliptically focused UV laser at the focal plane of the objective was monitored by fluorescence excitation of a suitable dye on a coverslip. Control of energy/pulse was achieved by orientation of a polarizer in the beam path. Predetermined numbers of pulses could be delivered through external triggering of the laser by use of National Instrument's data acquisition and control board. While the dimension of the line scissors could be easily varied by controlling the size of the aperture (VAP), control on orientation of the cuts required rotation of the cylindrical lens manually or by use of a rotatable stepper motor.

One of the purposes of the illustrated embodiment of the invention is to develop a device for fast patterned linear ablation of microscopic objects which is simple to operate and provides high throughput in a uniform manner.

Another purpose is to use the device for inducing DNA damage, cutting of microtubules, neuronal dissection, and optoporation of cells, just to name a few applications.

The fundamental principle exploited is that by shaping the pulsed laser beam into a linear profile via a cylindrical lens, line scissors can be achieved that provides simple and fast line patterned ablation as compared to scanning the beam with a motorized stage or scanning mirror. While the dimension of the line scissors can be easily varied by controlling the size of a circular aperture in the beam path, control of orientation of the line cuts requires rotation of the cylindrical lens achieved by use of a rotating mount.

The advantages of the present invention include (1) fast patterned linear ablation of microscopic objects, (2) simple operation, (3) high throughput in a uniform manner, and (4) less-expense. Uses of the invention include, but are not limited to: (i) induction of DNA damage, (ii) dissection of neuronal axons, (iii) micro-dissection of organelles such as microtubules, (iv) thinning of zona pellucida for use in reproductive medicine, (v) optoporation of exogenous material into cells.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 3a the targeted CHO cell away from the fiber tip (marked by arrow). In FIG. 3b movement of the cell toward the fiber tip due to the tweezing beam is shown. FIG. 3c shows trapping of the cell at the tip of the fiber. FIG. 3d-3e show transportation of the trapped cell to different location by maneuvering the fiber tip. FIG. 3f shows switching off the laser beam leading to movement of the cell away from tip. FIG. 3g shows trapping after laser is turned on. FIG. 3h shows lysis of cell, 200 ms after laser in pulsed mode at 200 fs, at 76 MHz is turned on. FIG. 3i shows complete lysis of cell after 800 ms. All images are at same magnification with a scale bar of 10 µm in FIG. 3a.

FIG. 4a shows a fiber tip positioned near the leading edge of the growth cone (circled). FIG. 4b shows an initial retraction at 5 min after irradiation of growth cone with CW near-infrared (NIR) fiber tweezers with a power: 42 mW. FIG. 4c shows enhanced growth within 15 min of irradiation. FIG. 4d shows change in direction of the neuronal growth cone after repositioning the fiber tweezers.

FIGS. 9d-9g show oscillation (arrows show direction of movement) of part of the optically bound chain at the loose end. The images in FIGS. 9b-9g are the same magnification with a scale bar of 10 µm shown in FIG. 9g.

FIG. 9h is a schematic of the near-field trapping and binding using small cone angle (e.g., 30°) tip. 30°) tip. Digitized images near-field trapped polystyrene particles at 68 mW beam power, after 1 min in FIG. 9i, 5 min in FIG. 9j, and 15 min FIG. 9k.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The short working distance of microscope objectives has severely restricted the application of optical micromanipulation techniques at larger depths. In the illustrated embodiment we show the first use of fiber-optic tweezers toward controlled guidance of neuronal growth cones and stretching of neurons. Further, by mode locking, the fiber-optic tweezers beam was converted to fiber-optic scissors, enabling dissection of neuronal processes and thus allowing study of the subsequent response of neurons to localized injury. At high average powers, lysis of a three dimensionally trapped cell was accomplished.

In the illustrated embodiment we demonstrate the use of a single fiber-optic axicon device for organization of microscopic objects using longitudinal optical binding. Further, by manipulating the shape of the fiber tip 10, part of the emanating light was made to undergo total internal reflection in the conical tip region, enabling near-field trapping. Near field trapping resulted in trapping and self-organization of long chains of particles along azimuthal directions (in contrast to the axial direction, observed in the case of large tip cone angle far-field trapping).

Figure 7A:
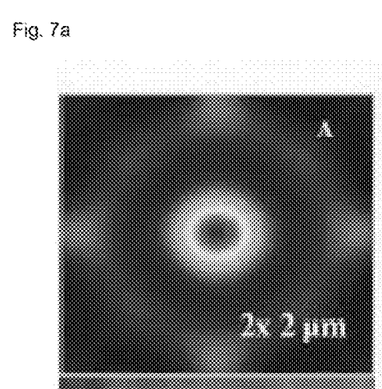
FIGS. 7a, 7b show in Color online XY-intensity distribution of the 800 nm beam transmitted through the fiber calculated at distances of 5 and 15 µm from the tip (fiber core size of 8 µm, refractive index of axicon as 1.5, cone angle of about 30°, and water as the medium).
Figure 7B:
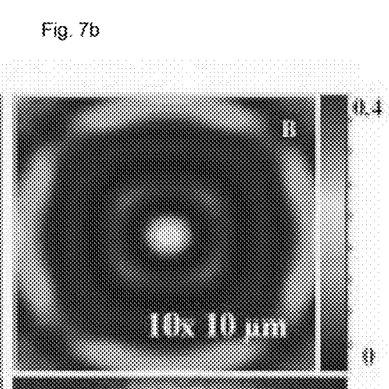
Figure 7C:
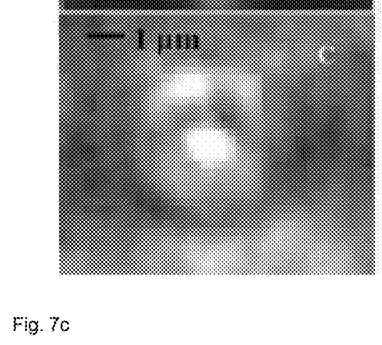
FIGS. 7c, 7d show measured beam profiles at distances of 5 and 15 µm.
Figure 7D:
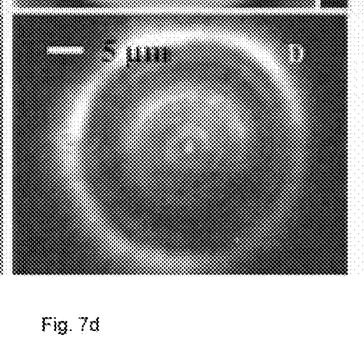

We disclose optical binding of microscopic particles trapped in a single fiber optic beam. For fabrication of the axicon tip with varying tip cone angle, a two-step chemical etching using hydrofluoric acid was employed as described below. FIGS. 7a-7d illustrate how Bessel-like beams having different propagation characteristics can be generated by engineering the axicon microstructure on the fiber. Starting with the fundamental mode of the fiber, $E_{fund} \approx \exp[-(X^2+Y^2)/\omega^2]$ where $\omega$ is the mode-field size, the electric field propagating from the tip can be described as $$E(x_o, y_o) = \frac{\exp(ikz)}{i\lambda z} \exp\left[i\frac{k}{2z}(x_o^2 + y_o^2)\right] \int_{-\infty}^{\infty}\int_{-\infty}^{\infty} \left\{ E(x_1, y_1) \exp\left[i\frac{k}{2z}(x_1^2 + y_1^2)\right] \right\} \exp\left[-i\frac{2\pi}{\lambda z}(x_o x_1 + y_o y_1)\right] dx_1\, dy_1, \quad (1)$$

where $E(x_1, y_1)$ is the field at the base of the microaxicon, which can be calculated using $E_{fund}$, and accounting for the phase acquired along the axicon-tip region. XY-intensity distribution of the 800 nm beam transmitted through the axicon tip, calculated at two Z distances from the tip (fiber core size, 8 µm; refractive index of axicon, 1.5; cone angle, about 30°), is shown in FIGS. 7a and 7b. FIGS. 7c and 7d show typical beam profiles measured at distances of 5 and 15 µm from the tip. The measured beam profiles showed Bessel-like beam profiles with few concentric rings. The scattering force in the axial direction is minimized by the Bessel-like beam as compared to the beam from a lensed/tapered fiber. Owing to this special property of the Bessel-Gauss beam (having a small high-intensity region along the Z direction), a relatively less diverging beam can achieve single beam optical tweezers as compared to Gaussian beam optical tweezers. In addition to an increase in propagation distance with a decrease in cone angle, transmittance of the beam through the fiber tip decreased substantially, which was attributed to an increase in TIR at the tip 10.

Figure 1A:
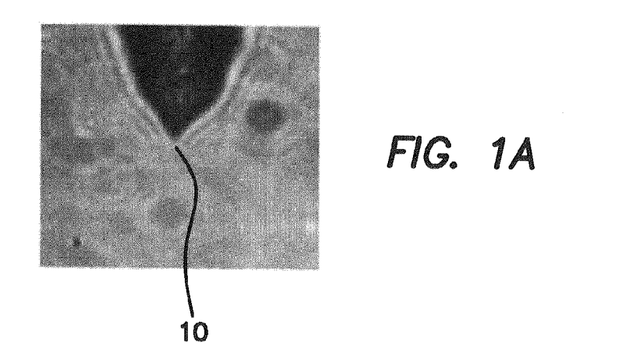
FIG. 1a is a microscopic image of a tapered tip with a 60° cone angle.
Figure 8A:
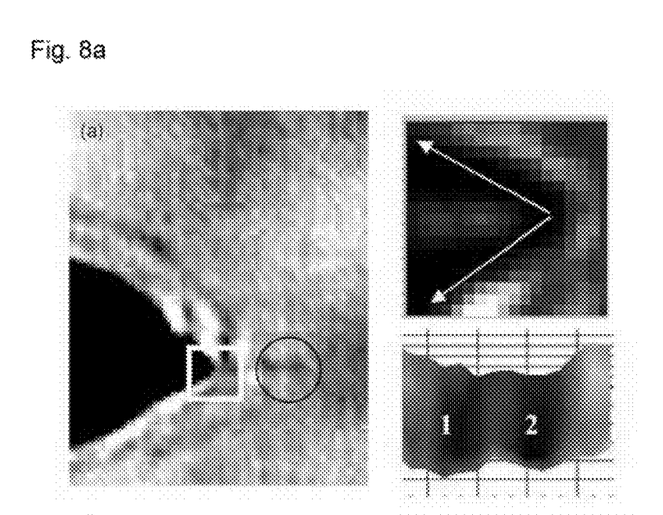
FIG. 8a show in Color online optical binding of two 1 µm polystyrene particles in the encircled region near the fiber tip. The top right inset of FIG. 8a shows magnified rectangular area of the tip. The inset in the bottom right of FIG. 8a shows a 3D intensity map of the two optically bound particles.

The experimental setup is described below in connection with FIGS. 1a and 1b. Two 1 µm polystyrene particles suspended in phosphate-buffered saline (PBS) were trapped and raised to a height of a few mm from the coverslip. FIG. 8a shows optical binding between two particles (in the encircled region) at a distance of about 3 µm from the tip. Analysis of images using cross-correlation techniques provided positions of particles with nanometer resolution. The contrast was increased by region-of-interest selection and thresholding. The bottom right inset in FIG. 8a shows a 3D intensity map of the two optically bound particles. The two optically bound particles remained almost at a fixed separation over the 10 min observation period. However, in the bound state, they were found to move in the axial direction within 3 to 6 µm. Translation of the fiber in three dimensions led to transportation of the (encircled) optically bound particles. The distance between the two particles decreased as they moved away from the tip 10. Tracking of particles (1 and 2) as the fiber tip (darkline) was translated is shown as an inset [FIG. 8b].

Figure 8B:
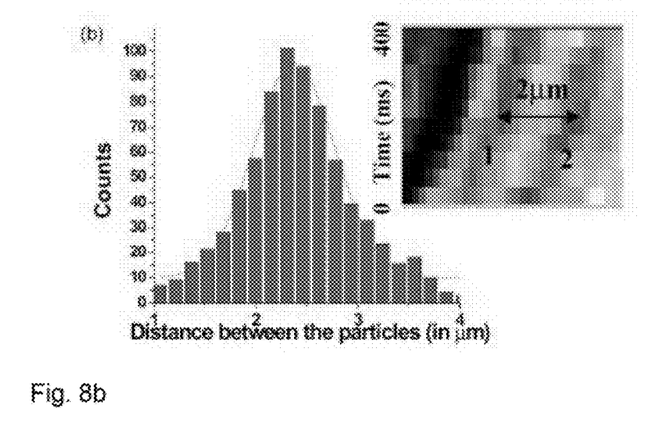
FIG. 8b is a measured histogram of the distance between centers of two 1 µm optically bound particles. The inset of FIG. 8b shows tracking of the two particles (1 and 2) as the fiber tip (dark line) is translated.
Figure 9A:
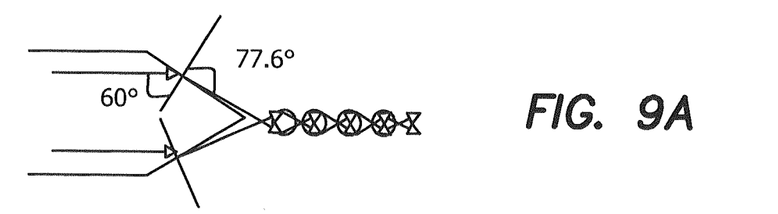
FIG. 9a shows in color online a ray optics schematic of longitudinal optical binding using large cone angle (e.g. 60°) tip. Optical trapping and binding leading to a chain of 1 µm polystyrene particles at 146 mW beam power is shown in FIG. 9b.

FIG. 8b shows the histogram of the separation between the optically bound particles measured over 30 s. FIG. 9a illustrates how far-field single fiber trapping and optical binding of a chain of microscopic particles could be achieved. For a cone angle of 60°, a truncated Bessel beam (power, 146 mW) trapping of polystyrene particles (diameter, 1 µm) was observed at a distance of about 5 µm from the tip 10.

For a fixed cone angle (e.g., 90°), trapping stiffness along the axial direction measured by the equipartition theorem method was found to depend on the size of the particle (2.0 pN/μm for 1 μm polystyrene versus 3.2 pN/μm for 2 μm polystyrene, for 60 mW trapping power). Similarly, trapping stiffness was found to depend on cone angle, e.g., 1.2 pN/μm for 60° cone angle and 2.0 pN/μm observed for a 90° cone angle tip, for a 1 μm particle trapped at a trapping power of 60 mW. This is due to the longer approximate 5 μm propagation distance of the Bessel beam generated by the 60° tip. This ensured transverse trapping of more particles along the axial direction.

Figure 9B:
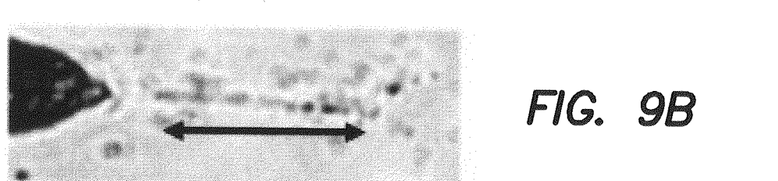
Figure 9C:
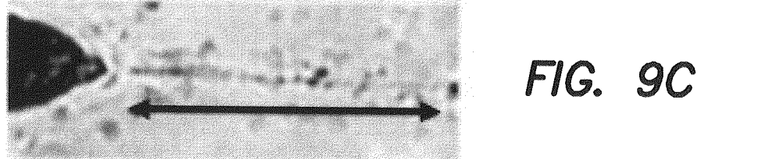
FIG. 9c shows accumulation of particles in a long chain about 50 µm after 15 min.
Figure 9D:
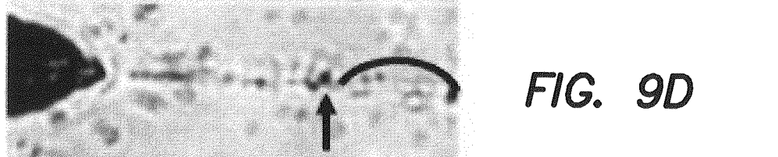
FIGS. 9d-9g show oscillation (arrows show direction of movement) of part of the optically bound chain at the loose end. The images in FIGS. 9b-9g are the same magnification with a scale bar of 10 µm shown in FIG. 9l.
Figure 9E:
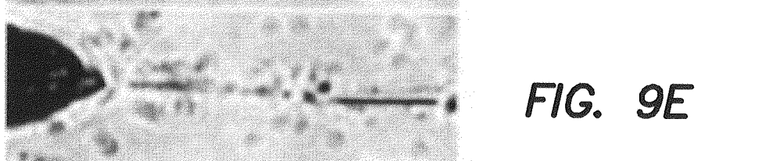
Figure 9F:
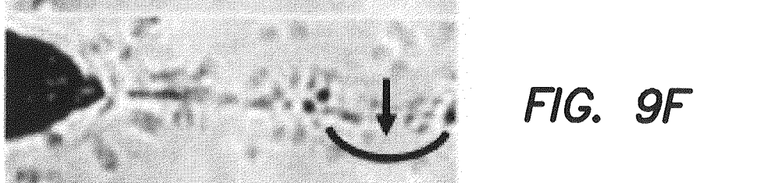
Figure 9G:
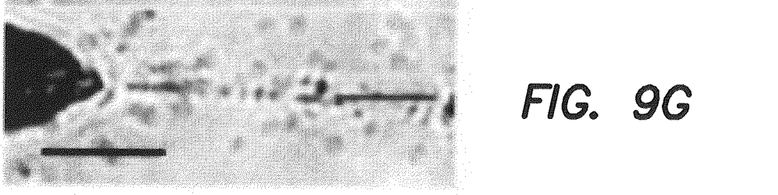
Figure 9H:
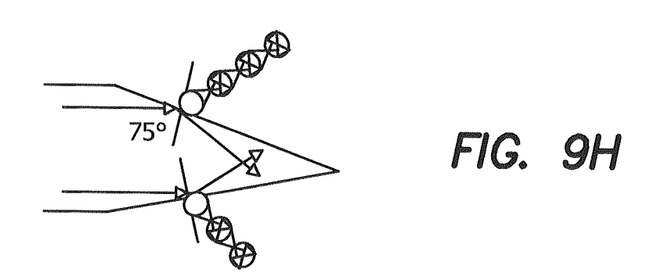
FIG. 9h is a schematic of the near-field trapping and binding using small cone angle (e.g., after a 15 min. duration.

FIG. 9b shows arrangement of a chain of approximately 20 particles along the beam propagation direction. This can be attributed to longitudinal optical binding where each trapped particle acts as a lens to trap a subsequent particle near its focal point as shown in FIG. 9a. The difference between the Bessel-Gauss beam generated by the axicon-tip fiber and the conventional Bessel beam is the propagation distance. A conventional Bessel beam (focused through a MO) has a large propagation distance and therefore low axial-trapping stiffness, leading to two dimensional (2D) optical trapping. The optically bound chain could be displaced by translation of the fiber. Over a 15 min period, more particles aligned along the axial direction as shown in FIG. 9c. During the transverse motion of the long chain (achieved by movement of the fiber), when an obstacle [particles adhered to the glass substrate, marked by arrow in FIG. 9d] was encountered, the loose end of the optically bound chain oscillated around the obstacle as shown in FIGS. 9d-9g. Though use of a larger cone angle) (90°) led to more axially stable 3D Bessel beam trapping, the optically bound chain was shorter compared to the smaller cone angle) (60°) tip. In order to achieve near-field trapping, the cone angle was made small enough)(≤30°) that a high percentage of the beam underwent TIR at the tip-water interface as shown in FIG. 9h. Since the strength of an evanescent wave decays rapidly with the distance from the place where it is generated, trapping volume is significantly reduced. The incidence critical angle for TIR is calculated to be about 63° (refractive index of the tip/water, 1.5/1.33) using Snell's law, which corresponds to a tip cone angle of 54°. Assuming all the rays to be parallel, none of the laser beam should exit a 30° cone angle tip.

Figure 9I:
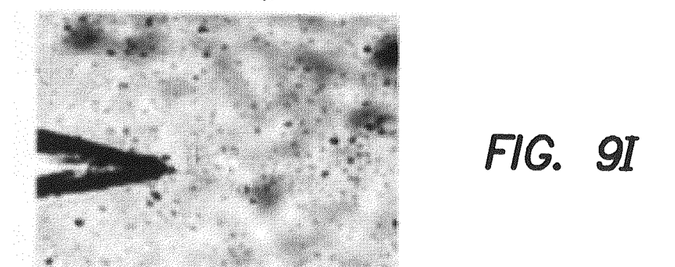
Figure 9J:
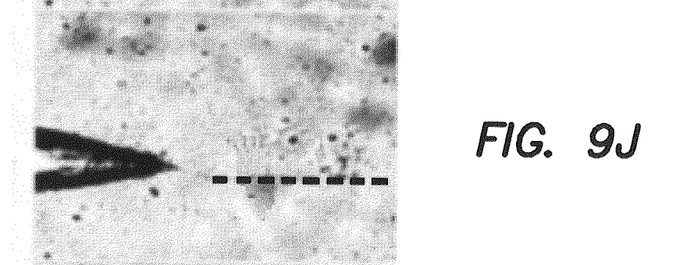
Figure 9K:
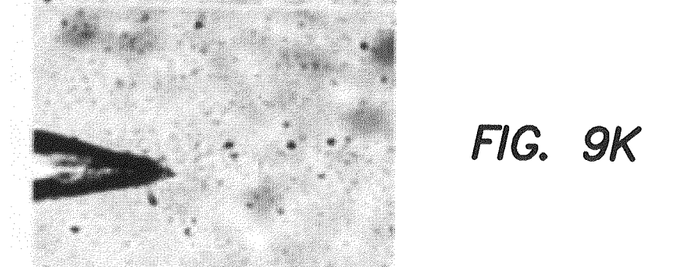
Figure 9L:
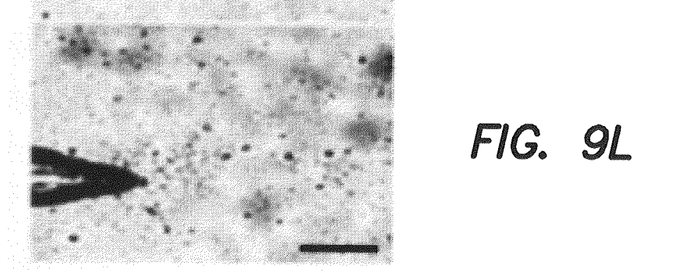
FIG. 9l shows the dispersion of the chain after the laser is turned off. Images in FIGS. 9i-9l are the same magnification with a scale bar of 20 µm shown in FIG. 9l.

However, imperfection in the tip and the fact that not all rays inside the single-mode fiber travel in straight lines leads to leakage of the beam. In our case, stable far-field trapping in the axial direction was rarely observed as shown in FIGS. 9i-9k since a small amount of laser power came out in the axial direction. Additionally, the propagation distance became longer, about 8 μm, adding to the instability. However, near-field trapping at the interface between the tip and the water led to better trapping and thus self-organization of long stable chains of particles along the azimuthal directions. Owing to the exponentially decaying evanescent field at the site of TIR, the closest trapped particle was found nearer to the surface of the tip in contrast to a few micrometers in the far-field case as shown in FIGS. 9a-9g. Azimuthal binding of trapped particles may be affected by whispering gallery mode excitation in the beads. The azimuthal angles, at which the optically bound chains are formed, were found to vary from 30° to 75° as shown in FIG. 9c. Some of the near-field induced optically bound chains (1 and 4) lengthened as shown in FIGS. 9i-9k over a period of time and became highly stable, while others at smaller azimuthal angles (2 and 3) shortened. Switching off the laser beam led to disorganization of the particles as shown in FIG. 9l. Metallization of the tip to enhance the evanescent field by the surface plasmon effect resulted in heating effects leading to convection and bubble formation.

It can now be appreciated that by shaping the axicon tip cone angle, single fiber optical trapping and binding in the far field as well as near-field was achieved, leading to organization of microscopic particles. Since the trapping force on metallic particles in the Rayleigh regime is higher as compared to dielectric particles, the axicon fiber can also be used to organize metallic nanoparticles and to study optical binding. The proposed noninvasive axicon-tipped fiber can be used in multifunctional mode for in-depth trapping as well as for excitation of fluorophores and detection of back reflected light/fluorescence.

Turn now and consider the manipulation of mammalian cells using a single-fiber optical microbeam. We show that by microshaping of the axicon fiber tip, effective three-dimensional trapping and micro-dissection is possible. We demonstrate the use of the fiber-optic tweezers for neuronal stretching and directed axonal growth guidance and fiber-optic scissors for dissection of neuronal growth cones and rapid cellular lysis.

Consider first the fabrication of an axicon-tip fiber. A single-mode optical fiber appropriate for 800 nm was used for preparing the axicon-tip fiber. One end of the mechanically cleaved bare single-mode fiber was dipped into 48% hydrofluoric (HF) acid containing a protective layer, e.g., Toluene, at the top. As is known in the art, the cone angle of the fiber tip is determined by the contact angle of HF with the fiber. The etching process is self-terminating, and the cone angle is influenced by the liquid used as a protection layer. The small cone angle fiber tip has been used earlier for in-depth trapping of low-index microscopic objects.

For varying the tip cone angle over a wider range, e.g., for 60° and 90°, and for mechanical rigidity, a two-step etching technique was employed. After the first selective chemical etching step, the tapered region has a cone angle of 30°, and the diameter at the end of the fiber is found to be about 40 μm. The etching time was 100 min. The second step with a selective etching solution having higher volume ratio of $NH_4F$ results in a sharp apex with a cone angle of about 90° with an etching time of about 140 min. The shape of the tip was optimized considering different experimental conditions. For example, while using it (in an almost horizontal plane) for neuronal growth enhancement, by lengthening the fiber tip region, contact between the cladding of the fiber and the substrate on which cells were grown could be avoided. FIG. 1a shows a typical axicon-tip fiber 10. The scanning electron microscopy, SEM, imaging of the fiber tip 10 shows that reproducible high-quality fiber tips 10 are produced by this method.

Figure 1B:
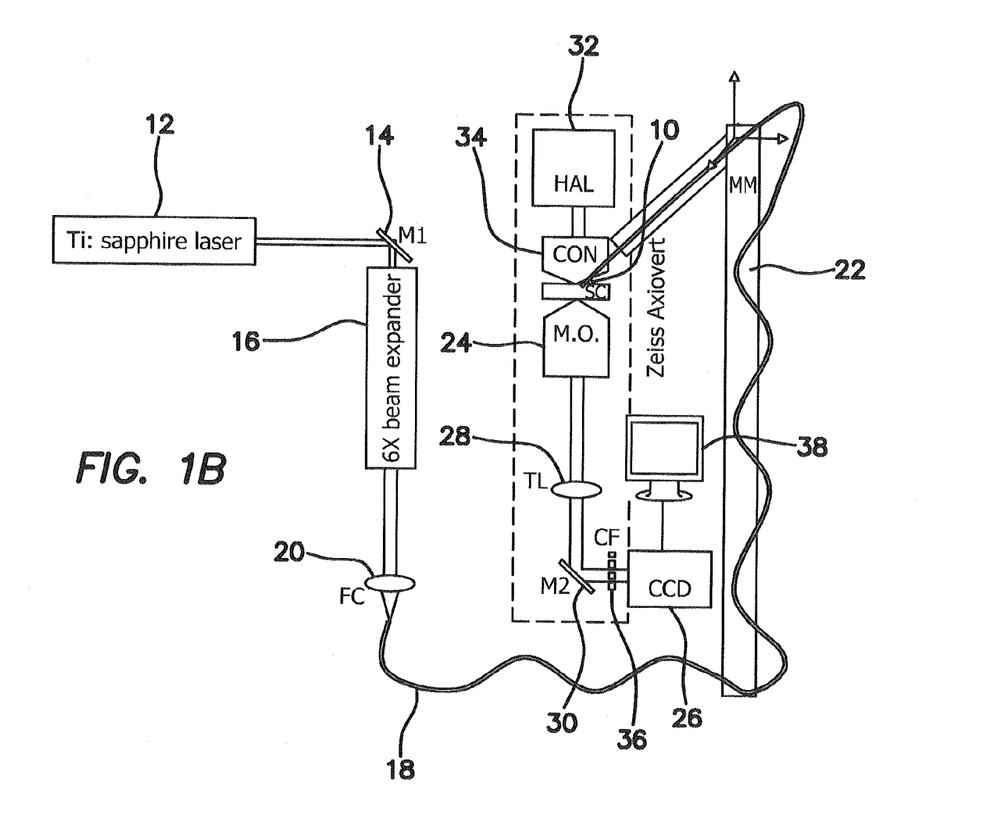
FIG. 1b is a schematic of the experimental setup wherein the illustrated embodiments are demonstrated.

The experimental setup is schematically depicted in FIG. 1b and is comprised of a TEM00 mode output of Ti:Sapphire laser 12 (780 nm, Coherent, Inc., Santa Clara, Calif.). The beam is reflected by mirror 14, M1, and expanded using a 6× beam expander 16 and coupled to the single-mode optical fiber 18 using a 20× objective 20 (FC). The tip 10 of the fiber 18 was mounted on a mechanical micromanipulator 22 (MM) in order to have 3-D movement control. In mode locking, the pulse duration is about 200 fs at frequency 76 MHz as measured by the manufacturer using autocorrelation. The spectral width measured using a spectrometer, (Model No. SM24, CVI Spectral Products, Putnam, Conn.) of the mode-locked laser beam coming out of the fiber 18, which had a length of 80 cm, was found to decrease to about 1.1 nm, implying broadening of the pulse. A 40× microscope objective 24 (M.O.) was used to image the beam profile as well as manipulation events onto the CCD camera 26 using a 200-mm focal length tube lens 28 and mirror 30. The sample chamber was transilluminated using a halogen lamp 32 through a condenser lens 34. An infrared (IR) cutoff filter 36 (CF) was used to block the laser beam from reaching the CCD camera 26. Images of the manipulation of objects were digitized using a frame grabber and computer 38. By moving the objective 24 for a range of 10 μm with a resolution of 2 μm, a series of images of transverse beam profiles were recorded for different tip cone angle fibers.

To determine the calibration of the trapping stiffness ($K_{trap}$) of fiber optic tweezers, we used the equipartition theorem method, $K_{trap} = \frac{1}{2} K_B T / \langle X^2 \rangle$, where $K_B$ is the Boltzmann constant, $\langle X^2 \rangle$ is the average of the square of the movement, and T is the temperature of the medium in which the particle is suspended. The chief advantage of this method is that knowledge of the viscous drag coefficient is not required and therefore neither is the particles geometry nor fluid viscosity. Polystyrene beads of 2-μm diameter were trapped and used for calibration of the fiber optic tweezers. The positions of the particle in the trap were detected using a centroid detection method. A software program on LabView platform was developed for quick analysis of a large number of images. Region of interest (ROI) selection and thresholding was carried out in order to reject background images.

Consider now the cell culture used in the illustrated embodiment. NG108 Neuroblastoma and Chinese hamster ovary (CHO) cells were obtained from American Type Culture Collection (Manassas, Va.). These were grown in Dulbecco's modified Eagle medium (DMEM) and Rosewell Park Institute medium (RPMI) supplemented with 10% fetal bovine serum, respectively (Invitrogen, Carlsbad Calif.). Cultures were maintained at 37° C. with 5% $CO_2$ supplementation. For cells to be trapped or stretched in the single-fiber optical stretcher, single-cell suspensions (CHO and NG108) were obtained by incubating the cells with 0.25% trypsin-EDTA solution at 37° C. for 4 min. After detaching, the activity of trypsin-EDTA was diluted by adding fresh culture medium. This treatment causes the cells to stay suspended as isolated cells for a few hours. The neuronal growth cone guidance experiments were performed at 37° C. Use of external $CO_2$ supplementation was avoided by use of pH-stabilized medium (through addition of 10 mM Hepes) in the neuron growth and dissection experiment.

Figure 2A:
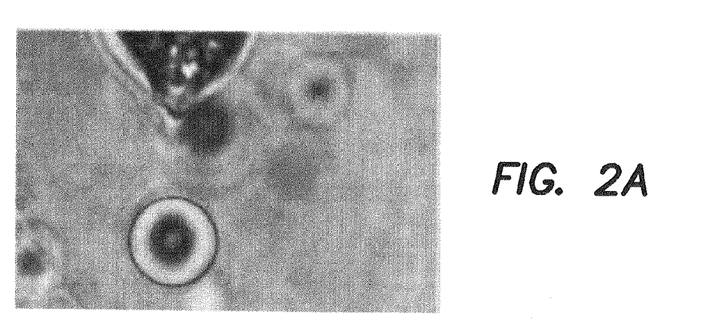
FIG. 2a is a microscopic image of a trapped 2-µm polystyrene particle (circled).
Figure 2B:
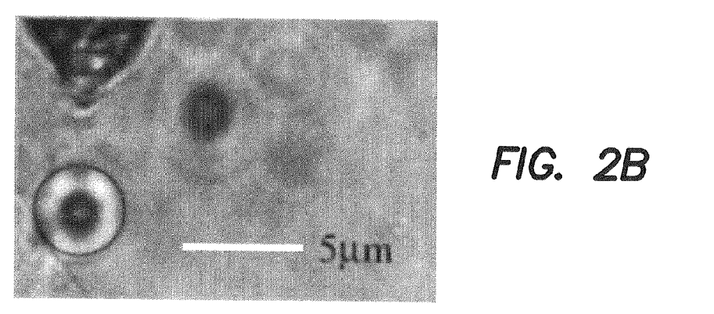
FIG. 2b is a microscopic image of the particle of FIG. 2a showing transportation of the trapped particle by maneuvering the fiber tip.
Figure 2C:
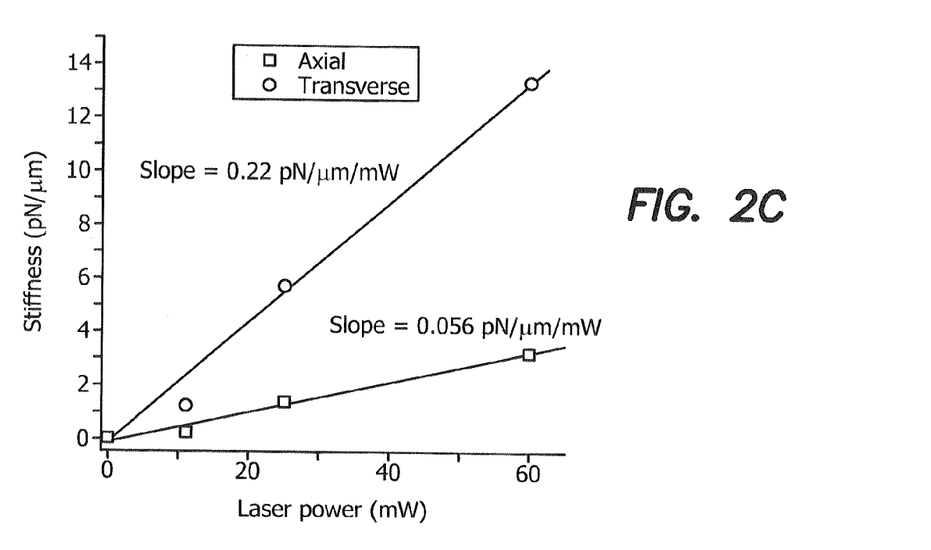
FIG. 2c is a graph of the measured stiffness along axial and transverse directions for the 2 µm particle as a function of trap beam power.

Consider now the measurement of transverse and axial trapping stiffness. FIG. 2a is a microphotograph which shows 3-D trapping of a polystyrene particle (refractive index=1.59, diameter 2 μm) using a 90° cone angle fiber tip. Translation of the fiber led to transportation of the particle as comparatively shown in the microphotograph of FIG. 2b. FIG. 2c is a graph which shows measured transverse trapping force at different trap beam powers for the 2-μm polystyrene particle. For a fixed beam power, the transverse trapping stiffness was found to be quite high, about 5.7 pN/μm at beam power of 25 mW as compared to the axial trapping stiffness of 1.4 pN/μm for the 2-μm polystyrene particle. The slope of the graphs for the transverse and axial directions was found to be 0.056 and 0.22 pN/μm/mW, respectively.

Figure 3A:
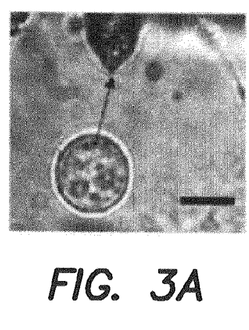
FIGS. 3a-i are microscopic time-lapse digitized images of trapping, transport, and lysis of a biological cell (CHO cell) using axicon tip single-fiber tweezers and scissors with a cone angle of 60°, power pf 95 mW.
Figure 3B:
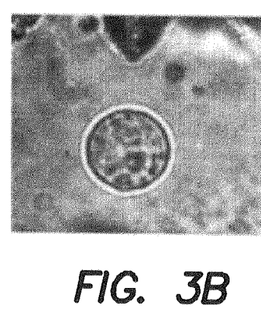
Figure 3C:
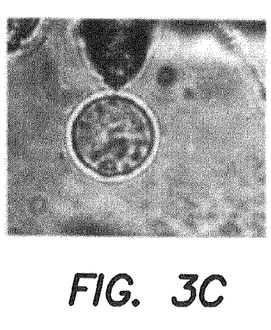
Figure 3D:
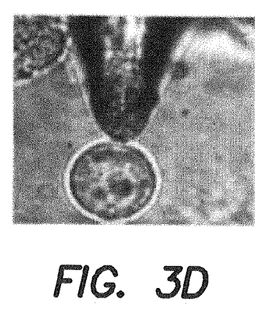
Figure 3E:
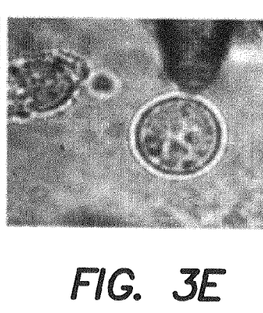
Figure 3F:
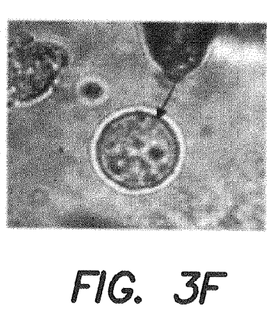
Figure 3G:
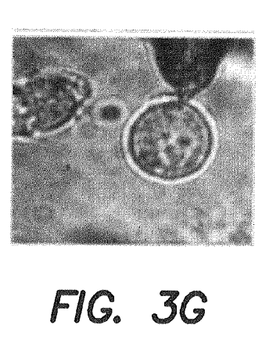
Figure 3H:
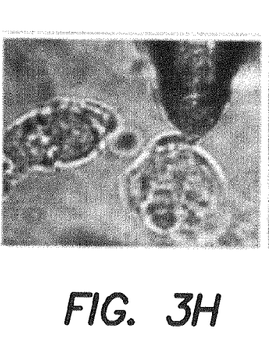
Figure 3I:
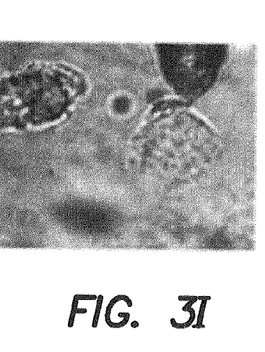

Turn now to the trapping and lysis of mammalian cells. In FIG. 3, we show how a single axicon-tip fiber can be deployed to perform optical trapping as well as lysis of biological cells. The cell (CHO), distant from the fiber tip 10 marked by an arrow in FIG. 3a, is attracted toward the fiber tip 10 in FIG. 3b at a power of 95 mW and was stably trapped very close to the axicon tip 10 as shown in FIG. 3c. The trapped cell could be transported to a new location as depicted by comparison of FIGS. 3d and 3e by maneuvering the fiber tip 10. Switching the laser beam on and off alternatively allowed the cell to move close as shown in FIG. 3g or away as shown in FIG. 3f from the fiber tip 10, ruling out the possibility of nonoptical attraction between the cell and the fiber tip 10. By mode locking the near-infrared (NIR) laser beam, femtosecond pulses of 200 fs, at 76 MHz could be delivered, and the same fiber probe could be used for lysis of the trapped cells as shown in FIGS. 3h and 3i in a time scale of 600±200 ms. This feature is required in many assays to immediately terminate biochemical reactions, thus preventing measurement artifacts resulting from the sample processing. By reducing the average power of the femtosecond fiber-optic microbeam, microinjection of impermeable exogenous materials into the trapped cells was also possible (not shown)

Figure 4A:
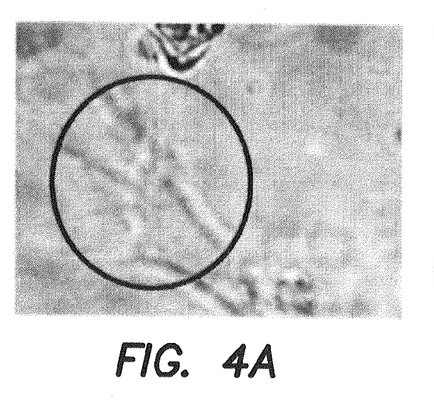
FIGS. 4a-4d are time-lapse digitized images of manipulation of NG108 neuroblastoma cells using single-fiber optical tweezers and scissors.
Figure 4B:
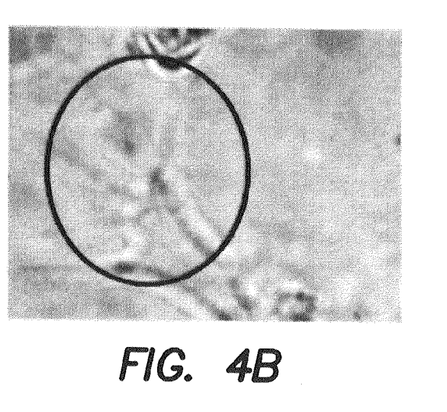
Figure 4C:
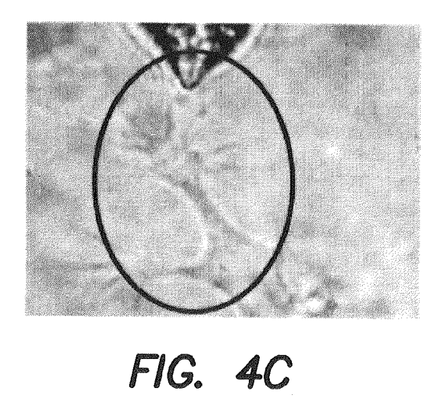
Figure 4D:
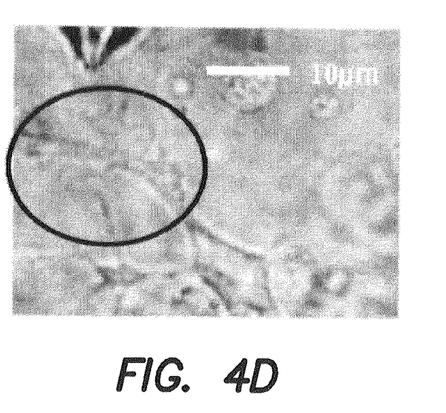
Figure 5A:
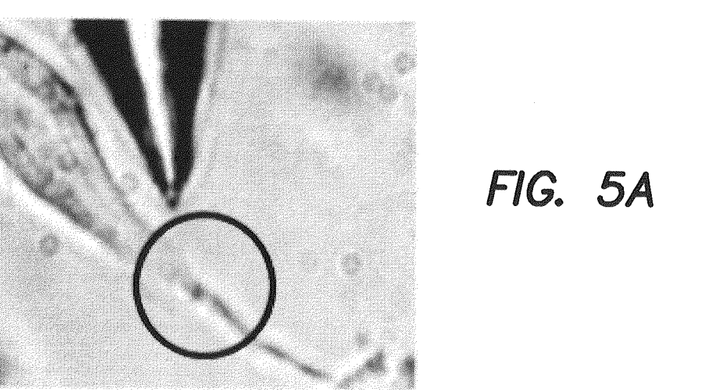
FIG. 5a shows a targeted location on the neural processes (circled) for nanosurgery.
Figure 5B:
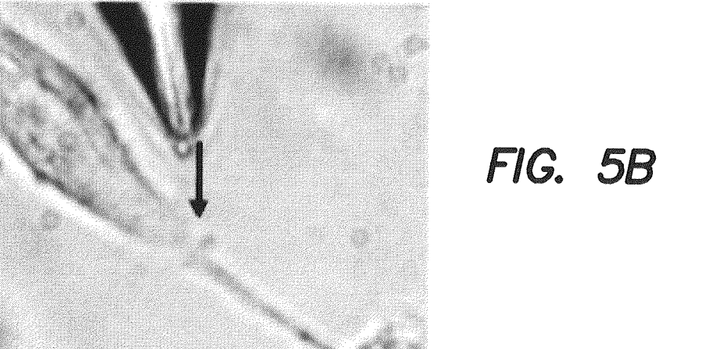
FIG. 5b shows a lesion made (marked by arrow) on the axon subsequent to laser nanodissection after mode locking the NIR tweezers laser beam at 42 mW.
Figure 5C:
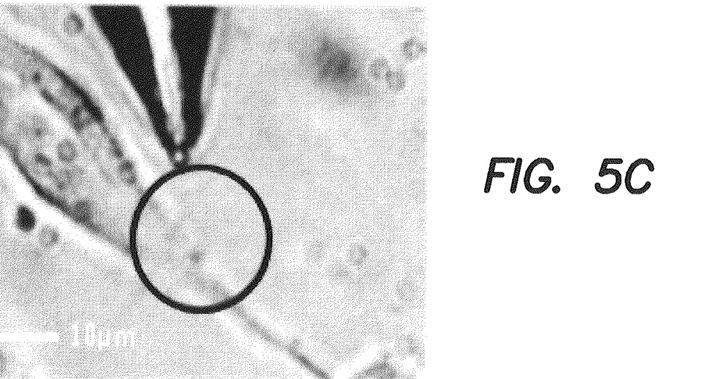
FIG. 5c shows resealing (in the circled region) of the neuronal process after 5 min of surgery.

Consider now controlled guidance and nanosurgery of neuronal growth cones. Manipulation of neuronal growth cones using single-fiber optical tweezers and scissors is illustrated in FIGS. 4a-4d. While irradiation on the growth cone as shown in FIG. 4a of an NG108 neuronal cell with a continuous wave (CW) NIR fiber tweezers at a power 42 mW led to initial retraction as shown in FIG. 4b, there was a significant enhancement of growth rate to 29±11 μm/h as compared to control cells which had a growth rate of 13±7 μm/h. The standard deviation around the mean was measured on 11 growth cones. The significance as measured by independent two-sample t-test was observed in FIG. 4c within 15 min of irradiation. This may be attributed to an induced accumulation of actins at the leading edge of the growth cone leading to an enhanced polymerization rate. Higher laser power in the range of 50 to 80 mW led to irreversible retraction. Therefore, the power was limited to 42 mW. A laser-induced temperature rise, leading to enhanced polymerization, can be ruled out since the power used here can only increase the local temperature by less than 1° C. However, photochemical, single- or two-photon effects of a focused 800-nm laser beam cannot be completely ruled out. It is also significant to note that we were able to guide and change the direction of the neuronal growth cone by repositioning the fiber tweezers at different locations as shown in FIG. 4d. The fact that 13 out of 18 growth cones changed direction by more than 30° following the fiber tip 10 as compared to 3 out of 14 in absence of the laser beam, we confirmed that the turning events are not placebo effect. These results are consistent with the theoretical simulations as shown in FIG. 4e, which showed that fiber-optic tweezers can exert directional dipole force and thus transport intracellular actin monomers/oligomers having a size of a few nm toward the center of the focused spot. By mode locking the NIR tweezers laser beam, at an average power of 42 mW, the fiber tweezers were transformed into fiber-optic laser scissors and were used to perform nanosurgery at desired locations on the neural processes as circled in FIG. 5a. FIG. 5b shows the lesion marked by arrow made on the axon subsequent to laser nanodissection, which was followed by a resealing process as shown in FIG. 5c. This microscopic-controlled nanodissection of neurons followed by a process of resealing and repair could serve as a useful model system for basic and applied studies on neuronal damage, repair, and regeneration.

Consider now the stretching of neuronal cells. In order to verify whether the fiber-optic tweezers can exert force on the membrane of the neuronal cell, NG108 cells were grown in suspension and subjected to fiber-optic tweezers. The cells were stretched by the combined action of two forces: an attractive gradient force due to the fiber-optic tweezers at high beam powers pulling the membrane and a scattering force on the membrane as reported in dual-fiber trapping. FIGS. 6a-6d illustrate stretching of NG108 neuronal cells in suspension using the single-fiber optical stretcher. The spherical NG108 neuroblastoma cell in suspension in FIG. 6a, became a tear drop in FIGS. 6b and 6c with elongation along the direction of propagation and compression along the orthogonal direction. Alignment of intracellular dark (high refractive index) material along the direction of laser beam propagation was also observed in FIG. 6c.

Figure 6A:
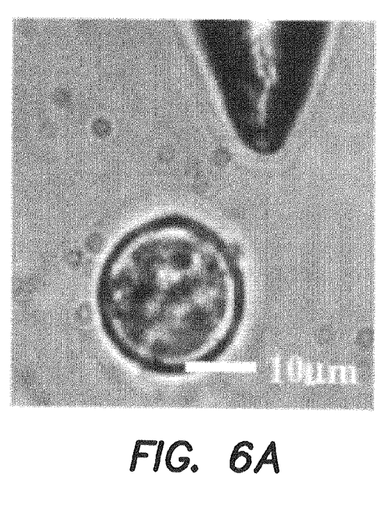
FIG. 6a shows the size of the NG108 neuroblastoma cell, in suspension increased from FIG. 6b, L1=21. 15±0.1 µm just before trapping to that shown in FIG. 6c, L1=23.00±0.1 µm along the beam axis at trapping power of 120 mW, and decreased in the perpendicular direction from L2=21.05±0.1 µm to L2=20.65±0.1 ρm.
Figure 6B:
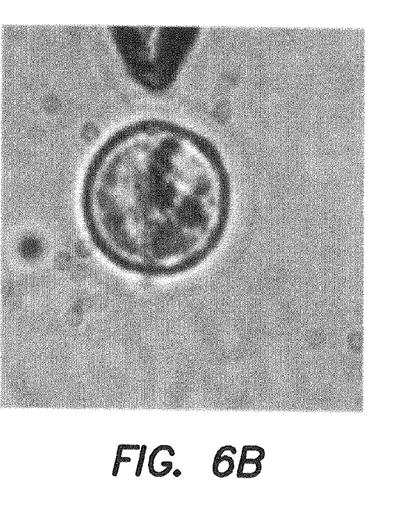
FIG. 6d shows that after reducing the power, the cell returned to its original shape within 120±40 ms. The values are standard deviation around mean values calculated over six measurements.
Figure 6C:
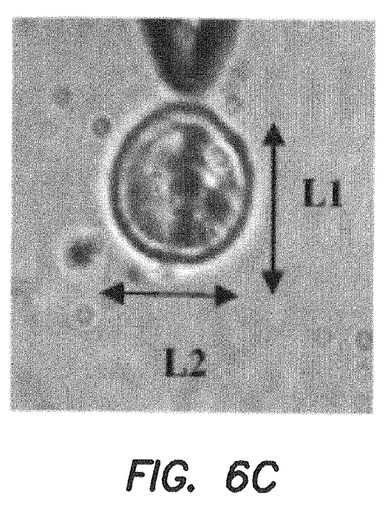
Figure 6D:
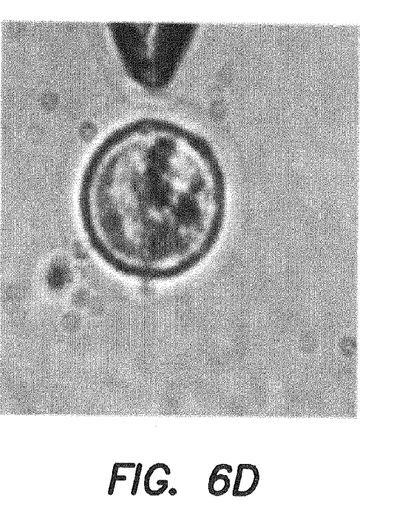

After reducing the power, the cell returned to its original shape as shown in FIG. 6d within 120±40 ms. Transportation of the cell along with the movement of the fiber tip 10 after the stretching operation could be carried out, ruling out tethering to the substrate. The observed stretching of a cell type with an extensive cytoskeleton suggests an even greater deformation potential for red blood cells, which lack an internal cytoskeleton. The single-fiber stretcher should be able to measure the viscoeleastic properties of different biological cells and thus monitor the progress of diseases or chemicals that affect the cytoskeleton. It also has an advantage over a dual-fiber optical stretcher because it avoids the crucial requirement of fiber alignment.

Therefore, it can now be appreciated that single-fiber optical trapping in the far and near field was made possible by shaping the axicon-tip cone angle. The fiber-optic tweezers could be used for trapping of cells as well as for controlling the growth rate and direction of neuronal growth cones. Further, single-fiber optical stretching of neuronal cells, in suspension, could be achieved by the combined action of attractive gradient and scattering forces on the cell membrane. By mode locking, the same laser beam coupled to the micro-axicon-tipped fiber could be transformed to optical scissors, enabling nanosurgery of neuronal growth cones. In addition, at high average powers, optical scissors were employed for lysis of a three-dimensionally trapped cell in a fraction of a second. The noninvasive micro-axicon tipped optical fiber can be used in multifunctional mode for in-depth trapping, stretching, rotation, sorting, microinjection, and ablation as well as for excitation of fluorophores and other light-activated ion channels. The depth attainable by optical micromanipulation not only is enhanced by a single microfabricated fiber device, but also this technology could lead to sophisticated sensing and imaging capabilities that can be applied to live cells.

It can thus now be readily appreciated that the illustrated embodiments of the invention include an apparatus for use with a laser comprising: a single optical fiber having a distal end and being optically coupled to the laser; and an axicon lens optically coupled to and terminating the single optical fiber to form a microscopic distal tip to provide a spatially shaped elongated laser focused spot for microprocessing and/or microdissection of a microscale object.

The axicon lens is integrally formed in the distal end of the single optical fiber or discretely formed apart from the distal end of the single optical fiber.

The axicon lens is arranged and configured to provide a linear profile to the spatially shaped elongated laser focused spot.

The apparatus further comprises a rotational stage coupled to the distal tip of the single optical fiber, a pulsed NIR laser and a continuous wave UV or NIR laser for producing an elongated beam both of which are optically coupled to the single optical fiber, wherein orientation of the elongated beam is controlled by the rotational stage.

The axicon lens has a focal plane and the focused spot has a length, and further comprising a variable aperture disposed at the focal plane of the axicon lens in order to control the length of the focused spot.

The apparatus further comprises an excitation source of light for fluorescent excitation combined with the pulsed NIR laser and a continuous wave UV or NIR laser.

The axicon lens has a predetermined cone angle selected at an angular cone angle to provide optical trapping and binding in the far field as well as near-field of the distal tip of the single optical fiber. In one embodiment the predetermined cone angle is approximately 30° or less. In another embodiment, the predetermined cone angle is approximately 90°.

The illustrated embodiments can now be understood to also include within their scope a method comprising the steps of: generating a pulsed or continuous laser beam or superposition of pulsed and continuous laser beams; controllably spatially shaping the laser beam or beams; selectively orienting the laser beam or at least one of the laser beams if spatially shaped; selectively moving the laser beam or beams via movement of a single optical fiber terminated with the axicon lens; and applying the oriented, spatially shaped laser beam via the single optical fiber terminated with the axicon lens to a living or nonliving microscopic object for manipulation, micro-dissection, alteration/ablation, and excitation of the living or nonliving microscopic object.

The step of controllably spatially shaping the laser beam or beams comprises the step of shaping the laser beam or beams into a linear profile via the axicon lens to provide line scissors that provides line patterned ablation.

The laser beam or beams has a beam path and the step of shaping the laser beam or beams into a linear profile comprises the step of controlling a size of a circular aperture in the beam path to control a dimension of laser line scissors.

The laser beam or beams has a beam path and the step of selectively orienting the laser beam or at least one of the laser beams if spatially shaped comprises the step of controlling an orientation of a line cut by rotation of the axicon lens in the beam path.

The step of generating a pulsed or continuous laser beam or superposition of pulsed and continuous laser beams comprises generating the pulsed laser beam by using a $N_2$ pulsed UV-laser for optical trapping of the object in suspension, and generating the continuous laser beam using a CW NIR laser aligned with the UV laser beam.

The method further comprises the steps of inducing DNA damage, cutting of microtubules, neuronal dissection, thinning of zona pellucida for use in reproductive medicine, or optoporation of cells.

The step of applying the oriented, spatially shaped laser beam via the single optical fiber terminated with the axicon lens to a living or nonliving microscopic object is arranged and configured to trap the object.

In one embodiment the object is a neuron or group of neurons and the step of applying the oriented, spatially shaped laser beam via the single optical fiber terminated with an axicon lens to a living or nonliving microscopic object is arranged and configured to control the growth rate and neuronal growth cones, to stretch neuronal growth cones, to perform nanosurgery, to rotate, sort, microinject, ablate, or excite a cell or group of cells.

It is also to be understood that the illustrated embodiment include a method comprising the steps of: generating a plurality of laser beams, each characterized by parametric characterization for a corresponding biomedical or biophysical functional use; controllably spatially shaping the plurality of laser beams according to the corresponding biomedical or biophysical functional use; and selectively applying the plurality of laser beams via a single optical fiber terminated with an axicon lens to a living or nonliving microscopic object for the corresponding biomedical or biophysical functional use.

The step of selectively applying the plurality of laser beams via a single optical fiber terminated with an axicon lens comprises the step of axial in-depth trapping of a living cell or group of cells in three dimensions over multiple dimensions commensurate with the size of the living cell or group of cells.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for use with a laser comprising:
a single optical fiber having a distal end and being optically coupled to the laser;
a rotational stage coupled to the distal tip of the single optical fiber, a pulsed NIR laser and a continuous wave UV or NIR laser for producing an elongated beam both of which are optically coupled to the single optical fiber, wherein orientation of the elongated beam is controlled by the rotational stage;
an excitation source of light for fluorescent excitation combined with the pulsed NIR laser and a continuous wave UV or NIR laser; and
an axicon lens optically coupled to and terminating the single optical fiber to form a microscopic distal tip to provide a spatially shaped elongated laser focused spot for microprocessing and/or microdissection of a microscale object.

2. The apparatus of claim 1 where the axicon lens is integrally formed in the distal end of the single optical fiber.

3. The apparatus of claim 1 where the axicon lens is discretely formed apart from the distal end of the single optical fiber.

4. The apparatus of claim 1 where the axicon lens is arranged and configured to provide a linear profile to the spatially shaped elongated laser focused spot.

5. The apparatus of claim 1 wherein the axicon lens has a focal plane and the focused spot has a length, and further comprising a variable aperture disposed at the focal plane of the axicon lens in order to control the length of the focused spot.

6. The apparatus of claim 1 where the axicon lens has a predetermined cone angle selected at an angular cone angle to provide optical trapping and binding in the far field as well as near-field of the distal tip of the single optical fiber.

7. The apparatus of claim 6 where the predetermined cone angle is approximately 30° or less.

8. The apparatus of claim 6 where the predetermined cone angle is approximately 90°.

* * * * *